(12) United States Patent
Green

(10) Patent No.: US 11,209,667 B1
(45) Date of Patent: Dec. 28, 2021

(54) EYEWEAR WITH HEADGEAR RETENTION DEVICES

(71) Applicant: Samuel J. Green, Charleston, SC (US)

(72) Inventor: Samuel J. Green, Charleston, SC (US)

( * ) Notice: Subject to any disclaimer, the term of this patent is extended or adjusted under 35 U.S.C. 154(b) by 186 days.

(21) Appl. No.: 16/266,910

(22) Filed: Feb. 4, 2019

Related U.S. Application Data

(60) Provisional application No. 62/626,154, filed on Feb. 5, 2018.

(51) Int. Cl.
| G02C 3/00 | (2006.01) |
| G02C 3/02 | (2006.01) |
| G02C 5/20 | (2006.01) |
| A61F 9/02 | (2006.01) |

(52) U.S. Cl.
CPC .............. *G02C 3/02* (2013.01); *G02C 3/003* (2013.01); *G02C 5/20* (2013.01); *A61F 9/027* (2013.01)

(58) Field of Classification Search
CPC .......... G02C 3/02; G02C 3/003; G02C 3/006; G02C 5/14; G02C 5/16; G02C 5/20; G02C 9/02; G02C 9/04; A61F 9/02; A61F 9/027
USPC .......................... 351/158, 140, 142, 148, 155
See application file for complete search history.

(56) References Cited

U.S. PATENT DOCUMENTS

| 3,703,750 | A | * | 11/1972 | Irwin, Jr. ............... | A42B 3/185 24/265 R |
| 4,276,657 | A | * | 7/1981 | Montesi ................. | A42B 3/185 2/10 |
| 4,796,308 | A | * | 1/1989 | Bourgeois .............. | A42B 3/185 2/10 |
| 4,991,236 | A | | 2/1991 | Pritchett | |
| 6,481,059 | B2 | | 11/2002 | Morris | |
| 6,637,074 | B1 | | 10/2003 | Morris | |
| 6,644,807 | B1 | * | 11/2003 | Hood ..................... | A42B 1/247 2/10 |
| 7,020,900 | B2 | | 4/2006 | Ngan | |
| 7,703,153 | B2 | | 4/2010 | De Taboada | |
| 8,210,676 | B1 | * | 7/2012 | Hunt ....................... | G02C 9/04 351/133 |
| 8,555,423 | B2 | | 10/2013 | Giroux et al. | |
| 2007/0226957 | A1 | * | 10/2007 | Lee-Holowka ....... | A45C 11/04 24/3.1 |
| 2008/0172775 | A1 | * | 7/2008 | Higgins ................. | A42B 3/185 2/422 |
| 2008/0250538 | A1 | * | 10/2008 | Saladino ................ | A42B 1/247 2/10 |
| 2010/0231851 | A1 | * | 9/2010 | Anhalt ................... | A42B 1/247 351/155 |
| 2015/0115008 | A1 | | 4/2015 | Griffith | |

* cited by examiner

*Primary Examiner* — Jordan M Schwartz

(74) *Attorney, Agent, or Firm* — Fish & Richardson P.C.

(57) ABSTRACT

Eyewear configured to retain a hat on a wearer's head is described herein. In one aspect, eyewear includes spectacles configured to be worn over eyes of a wearer. The eyewear also includes an elastic headband configured to fit around a head of the wearer. The elastic headband is attached to the spectacles. The eyewear includes two or more headgear retention devices attached to the headband and configured to be removably attached to a hat when the hat is worn on the head of the wearer and the headband is worn around the head of the wearer.

10 Claims, 7 Drawing Sheets

EYEWEAR WITH HEADGEAR RETENTION DEVICES

CLAIM OF PRIORITY

This application claims the benefit of U.S. Provisional Patent Application No. 62/626,154, entitled, "Sports Googles With Hat Retention Clips", filed on Feb. 5, 2018, the entire contents of which are hereby incorporated by reference.

BACKGROUND

People commonly wear hats or other headgear when playing sports and participating in other activities outdoors. High winds and some activities, such as riding a personal watercraft or motorcycle, commonly cause hats to fly off people's heads.

SUMMARY

This specification describes eyewear, e.g., sports goggles, configured to hold a hat on a person's head when the person is involved in physical activities and/or in windy conditions.

In general, one innovative aspect of the subject matter described in this specification can be embodied in eyewear that includes spectacles configured to be worn over eyes of a wearer. The eyewear can also include an elastic headband configured to fit around a head of the wearer. The elastic headband can be attached to the spectacles. The eyewear can also include two or more headgear retention devices attached to the headband and configured to be removably attached to a hat when the hat is worn on the head of the wearer and the headband is worn around the head of the wearer.

These and other embodiments can each optionally include one or more of the following features. In some aspects, the headgear retention devices can be attached to locations on the headband such that, when the headband is worn around the head of the wearer, at least one headgear retention device is located in front of a left ear of the wearer and at least one headgear retention device is located in front of a right ear of the wearer.

In some aspects, the spectacles are goggles. In some aspects, each headgear retention device is sewn into the headband. Each headgear retention device can be a garment clip that clips to the hat.

In some aspects, the spectacles can include a first headband attachment mechanism located on a first side of the spectacles and a second headband attachment mechanism located on a second side of the spectacles. The second side is opposite the first side. The headband can include two separate bands including a first band and a second band, each band having a first end and a second end. The first end of each band can attach to a respective one of the headband attachment mechanisms. The second end of the first band can be attached to a strap adjuster. The second end of the second band can include a hook-and-loop fastener for removably attaching the second band to the strap adjuster.

In general, another innovative aspect of the subject matter described in this specification can be embodied in a method for producing eyewear. The method can include attaching a first elastic band to a first side of spectacles and a second elastic band to a second side of the spectacles opposite the first side. One or more headgear retention devices can be attached to each of the first elastic band and the second elastic band. Each headgear retention device can be configured to be removably attached to headgear when the headgear is worn on the head of a person and the eyewear is worn around the head of the person. A tightening mechanism can be attached to at least one of the first elastic band or the second elastic band. The tightening mechanism can be configured to enable the person to adjust a tightness of the eyewear on the person's head.

These and other embodiments can each optionally include one or more of the following features. In some aspects, the spectacles are goggles.

In some aspects, attaching each headgear retention device can include sewing or stitching the headgear retention device onto or into the first elastic band or the second elastic band. Each headgear retention device can be a garment clip that clips to the headgear.

In some aspects, attaching the first elastic band to the first side of spectacles and the second elastic band to the second side of the spectacles can include attaching a first end of the first elastic band to a first headband attachment mechanism located on the first side of the spectacles and attaching a first end of the second elastic band to a second headband attachment mechanism located on the second side of the spectacles.

In some aspects, the tightening mechanism includes a strap adjuster. Attaching the tightening mechanism to at least one of the first elastic band or the second elastic band can include attaching a second end of the first elastic band to the strap adjuster, including passing the second end of the first elastic band through an aperture of the strap adjuster and attaching the second end of the first elastic band to a portion of the first elastic band that did not pass through the aperture of the strap adjuster.

In some aspects, the tightening mechanism includes a hook-and-loop fastener attached to the second elastic band.

In some aspects, attaching one or more headgear retention devices to each of the first elastic band and the second elastic band can include attaching a first headgear retention device to a first location on the first elastic band within a specified distance from the first side of the spectacles such that, when the eyewear is worn by the person, the first headgear retention device is located in front of a first ear of the person. Attaching one or more headgear retention devices to each of the first elastic band and the second elastic band can also include attaching a second headgear retention device to a second location on the second elastic band within a specified distance from the second side of the spectacles such that, when the eyewear is worn by the person, the second headgear retention device is located in front of a second ear of the person.

In general, another innovative aspect of the subject matter described in this specification can be embodied in a method of using eyewear. The method can include placing eyewear on a head of a person. The eyewear can include spectacles, two elastic bands, and one or more headgear retention devices attached to each elastic band. Each elastic band can have a first end attached to a corresponding side of the spectacles and a second end attached to a strap adjuster. The eyewear can be tightened on a head of the person. Headgear can be placed on the head of the person. Each headgear retention device can be secured to the headgear.

These and other embodiments can each optionally include one or more of the following features. In some aspects, each headgear retention device includes a clip. Securing each headgear retention device to the headgear can include opening each clip, putting a bottom portion of the headgear into an opening of the opened clip, and closing the clip such that the clip attached to the bottom of the headgear.

In some aspects, the spectacles are goggles. In some aspects, each headgear retention device is sewn or stitched into one of the elastic bands.

In some aspects, at least one of the elastic bands includes a hook-and-loop fastener that includes a patch of hooks and a patch of loops. Tightening the eyewear on the head of the person can include adjusting a position of the patch of hooks relative to a position of the patch of loops and pressing the patch of hooks against the patch of loops.

Particular embodiments of the subject matter described in this specification can be implemented so as to realize one or more of the following advantages. Eyewear described herein can retain headgear, such a hats, on people's heads even in high wind conditions and/or when the people are performing activities that could normally cause their headgear to fly from their heads. The combination of an elastic headband and headgear retention clips (or other headgear retention devices) located on either side (e.g., opposite sides) of the person's head and in front of the person's ears maintains the headgear in the appropriate position on the person's head without allowing wind to push the bill of the headgear up and out of position. For example, with the clips in this position, the front of the headgear is prevented from moving relative to the person's head. As the bill of a hat is most prone to being blow by wind and causing the hat to move when blown (e.g., wind blowing under the bill and pushing the bill of the hat upwards), the clips in position in front the person's ears and closer to the bill has a greater impact in preventing the hat from moving relative to clips being positioned further to the back of the hat.

The elastic headband provides additional support against movement of the headgear as the headband can be fitted more tightly around the person's head relative to inelastic headbands. An adjustable mechanism, e.g., a mechanism that includes hook-and-loop fasteners, enables the person to adjust the tightness of the elastic band even more to ensure that the elastic band is tight on the person's head, further reducing the ability of the headgear to move out of position due to wind.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

In general, the subject matter described in this specification relates to eyewear that attaches to hats (and other headgear) to prevent the hats from blowing off people's heads. The eyewear can include a headband, e.g., an elastic headband, that includes headgear retention devices that attach to hats. The eyewear can also include glasses, goggles, framed lenses, or other appropriate spectacles attached to the headband to be worn over a person's eyes. The headband can be worn around a person's head so that the spectacles are in front of the person's eyes. The headgear retention devices can be clips attached to the headband, e.g., stitched onto or into the headband. The headgear retention devices can be removably attached to the bottom of the headgear, e.g., to the bottom of the crown of a baseball cap, to hold the headgear in place on the person's head.

Figure 1A:
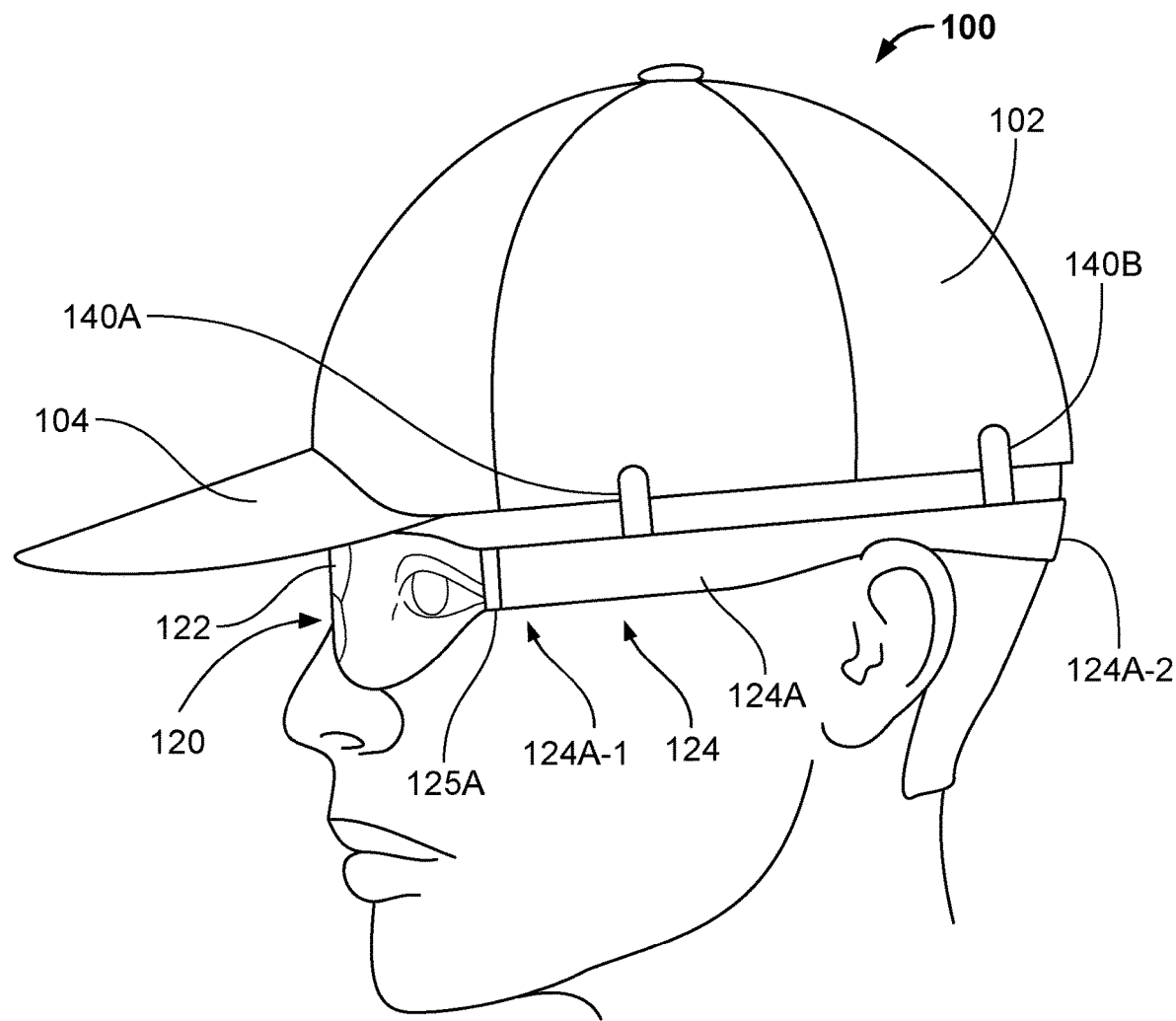
FIGS. 1A-1D are illustrations of a hat and example eyewear with headgear retention devices.
Figure 1B:
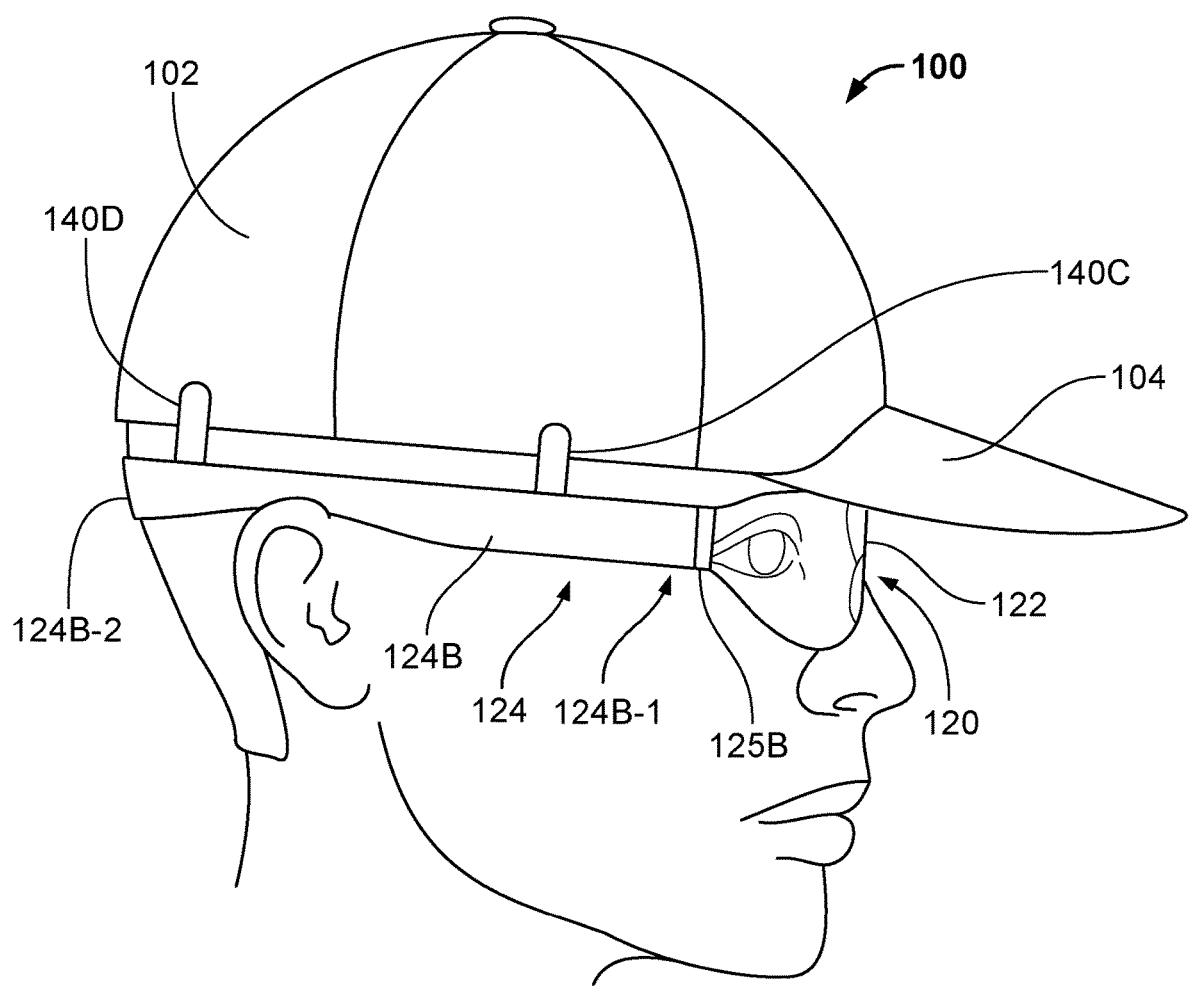
Figure 1C:
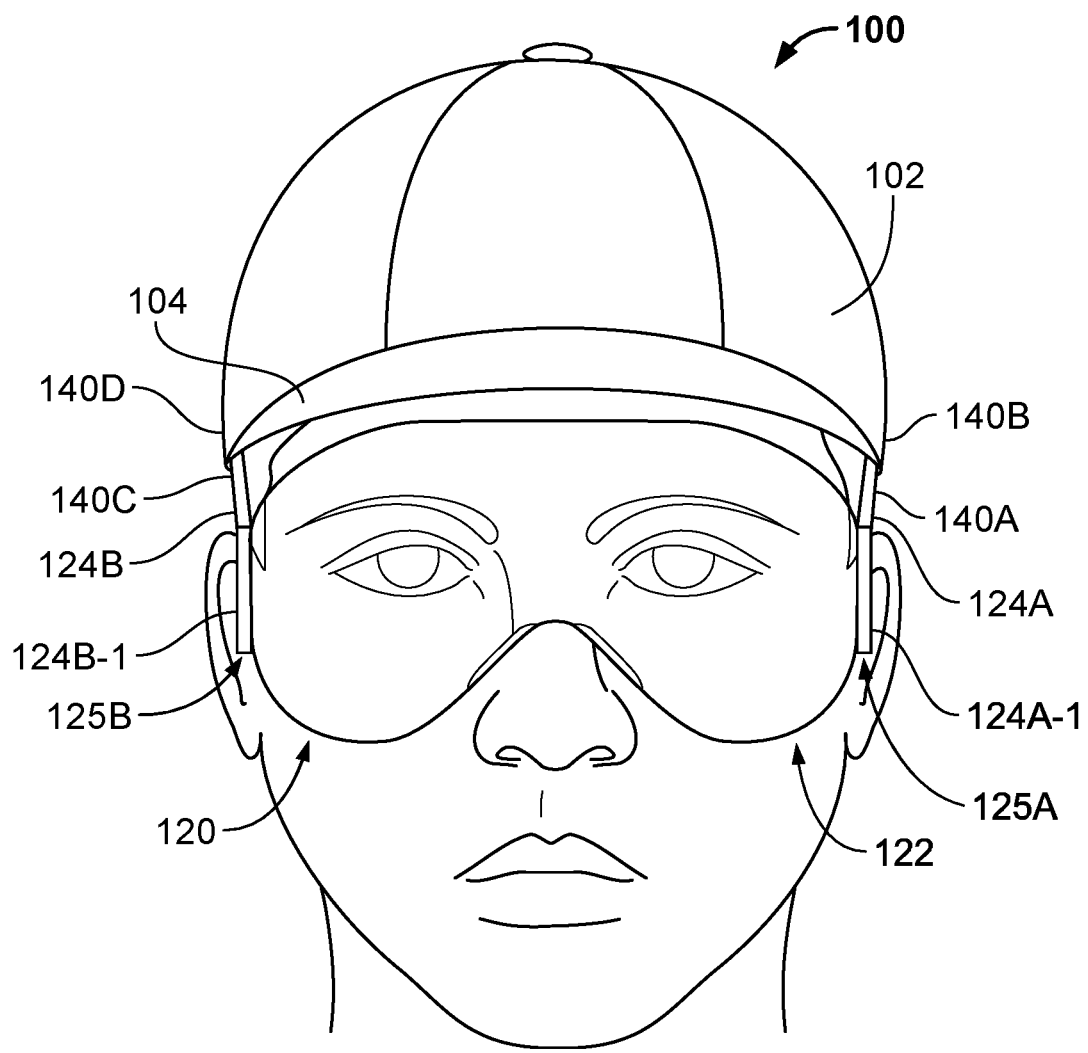
Figure 1D:
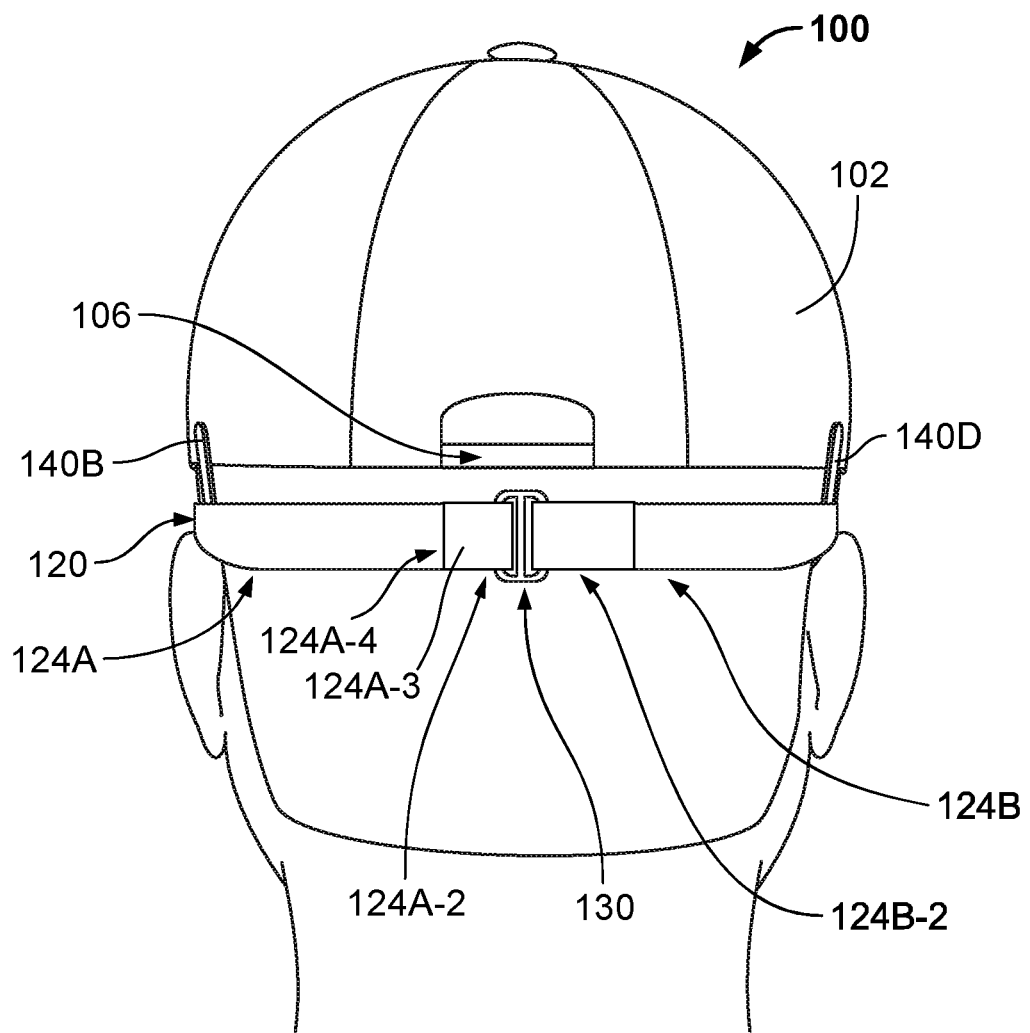

FIGS. 1A-1D are illustrations of a hat 100 and example eyewear 120 with hat retention devices 140A-140D. In particular, FIG. 1A is a view of one side of the hat 100 and eyewear 120; FIG. 2B is a view of the other side of the hat 100 and eyewear 120; FIG. 1C is a front view of the hat 100 and eyewear 120; and FIG. 1D is a back view of the hat 100 and eyewear 120. The relative dimensions in each figure are illustrative only and not necessarily to scale.

In this example, the hat 100 is a baseball cap with a crown 102, which can be made of one or more panels, a bill 104, and an adjustment strap 106 on the back of the hat 100. The eyewear 120 can also be used with other types of hats and headgear, such as visors, beanies, ivy caps, duckbill caps, berets, trucker caps, etc.

The eyewear 120 includes spectacles 122 and a headband 124. The spectacles 120 can be glasses, sunglasses, goggles, framed lenses, or other appropriate types of spectacles that are worn over a person's eyes. For example, the eyewear 120 can be sports goggles, e.g., skiing goggles, attached to an elastic headband. The headband 124 can be made of an elastic material so that the band 124 can fit tightly on a person's head. For example, the band can be made of nylon, polyester, spandex, a cotton blend, a nylon and polyester blend, and/or other appropriate elastic materials that are suitable to be worn on a person's head.

The headband 124 can be attached to either side of the spectacles 122. For example, either side of the spectacles 122 can include a headband attachment mechanism 125A and 125B that has an aperture (e.g., a rectangular-shaped aperture) through which a corresponding end of the headband 124 passes. The headband attachment mechanisms 125A and 125B can be apertures in the frame of the spectacles 122 that are configured to receive a headband 124.

Each end of the headband 124 can pass through its corresponding aperture and then be secured to a portion of itself that is not passed through the aperture, e.g., by stitching the end of the band to itself or using hook-and-loop fasteners. This prevents the end of the headband 124 from going back through the aperture. In other examples, the headband 124 is attached to the spectacles 122 using other attachment techniques, e.g., buttons, clips, adhesives, etc.

The headband 124 can be a single band or multiple bands. In this example, the headband 124 includes two bands 124A and 124B that are both connected to a strap adjuster 130 (FIG. 1D). One end 124A-1 of the band 124A can be attached to a side of the spectacles 122, e.g., by passing through an aperture of the headband attachment mechanism 125A and being attached to itself. The other end 124A-2 of the band 124A can be secured to the strap adjuster 130. Similarly, one end 124B-1 of the band 124B can be attached to a side of the spectacles 122, e.g., though an aperture of the headband attachment mechanism 125B on the opposite side of the spectacles 122 from the side to which the end 124A-1 of the band 124A is attached. The other end 124A-2 of the band 124A can also be secured to the strap adjuster 130.

One of the bands (e.g., the band 124A) can be attached to the strap adjuster 130 in a semi-permanent or permanent manner, e.g., such the band 124A cannot be easily removed from the strap adjuster 130 without a tool such as a knife or scissors. For example, an end 124A-2 of the band 124A can pass through an aperture of the strap adjuster 130 and be attached to itself, e.g., using stitching, adhesives, or another appropriate attachment mechanism. For example, as shown in FIG. 1D, a portion 124A-3 of the end 124A-2 is passed through the aperture of the strap adjuster 130 and attached to a portion 124A-4 of the band 124A that is not passed through the aperture of the strap adjuster 130. The other end 124A-1 of this band 124A can be attached to its side of the spectacles 122, as described above.

Figure 2:
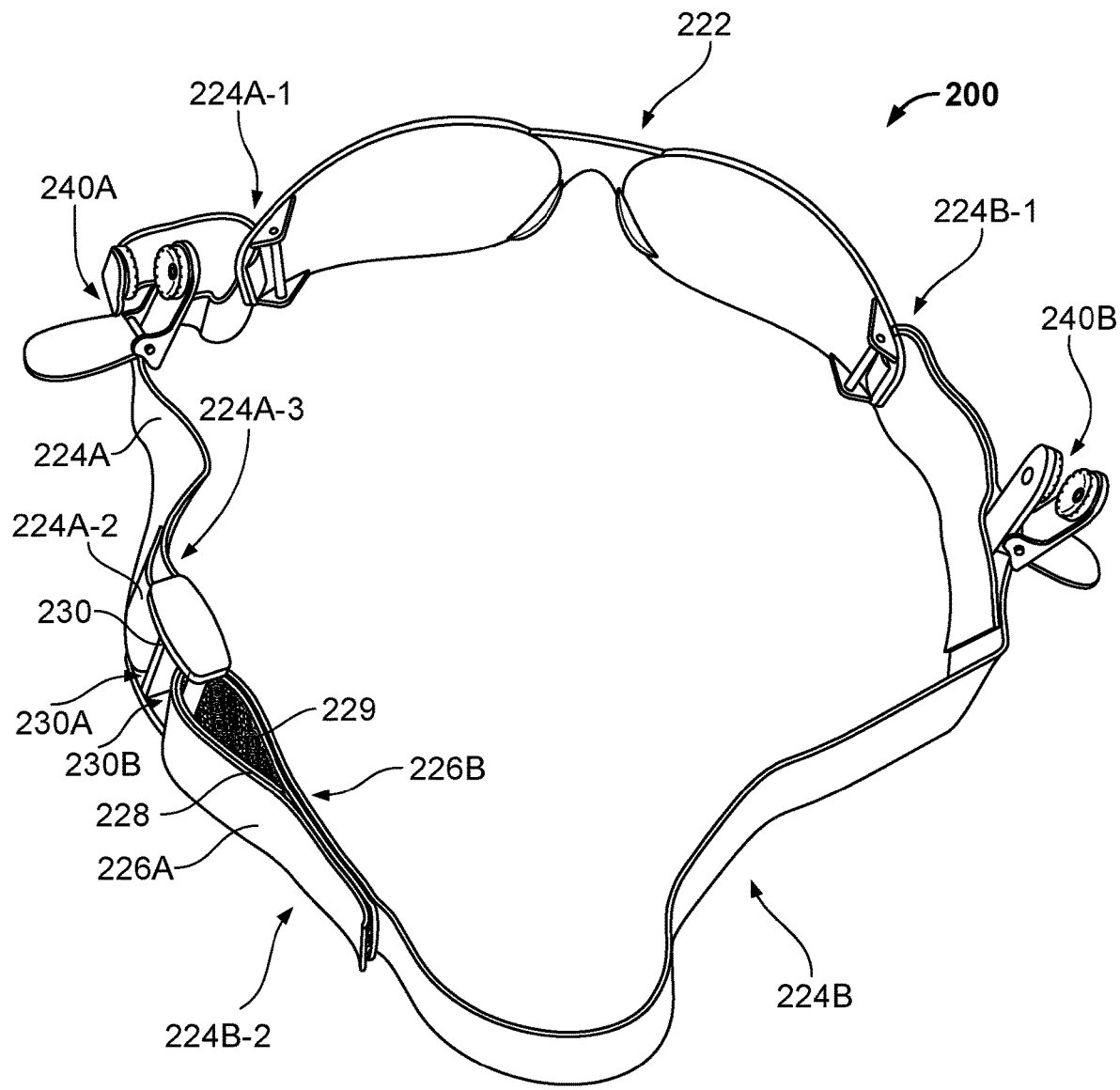
FIG. 2 is an illustration of example eyewear with headgear retention devices.

The other band, e.g., the band 124B, can be removably attached to the strap adjuster 130 in way that allows the tightness of the headband 124 to be adjusted and for the eyewear 120 to be easily removed from the person's head, e.g., without requiring any tools. For example, one end 124B-1 of the band 124B can be attached to its side of the spectacles 122. The other end 124B-2 of the band 124B can include a hook-and-loop fastener, e.g., VELCRO® Brand hook and loop, that enables the tightness of the headband 124 to be adjusted. For example, one side of the end 124B-2 of the band 124B can include a first patch of hooks, e.g., a fabric strip of hooks, and a second patch of loops, e.g., a fabric strip of loops. The first patch of hooks can pass through an aperture of the strap adjuster 130 and be pressed against the second path of loops. When the two patches are pressed together, the hooks of the first patch catch in the loops of the second patch, fastening the two patches temporarily. An example of a hook-and-loop fastener is illustrated in FIG. 2.

The strap adjuster 130 and the hook-and-loop fastener allows a person to adjust the tightness of the headband 124 for comfort and to better prevent the hat 100 from being blown from the person's head. In general, the tighter the headband 124 is on the person's head, the less chance the hat 100 has of being blown from the person's head. For example, if the headband 124 is too loose, wind can cause the hat 100 and eyewear 120 to be detached from the person's head.

The eyewear 120 includes headgear retention devices 140A-140D attached to the headband 124. The headgear retention devices 140A-140D are also removably attached to the hat 100, e.g., without using a tool. The headgear retention devices 140A-140D can be clips, such as garment clips, pacifier clips, suspender clips, lanyard clips, other appropriate types of clips capable of attaching to headgear. The clips can be plastic, metal, or another appropriate material. When attached to the hat 100, the headgear retention devices 140A-140D provide enough tension to keep the hat on the person's head in windy conditions, e.g., when wind blows under the bill 104 due to windy conditions or physical activity by the person wearing the hat 100. Using clips or other detachable headgear retention devices enables a person to quickly and easily attach and detach the eyewear 120 to and from the hat 100.

In some implementations, one or more of the headgear retention devices 140A-140D are clips that include teeth that provide additional tension on the hat 100 to prevent the hat 100 from being blown from the person's head. For example, at least some of the headgear retention devices 140A-140D can be alligator clips that include teeth.

In the illustrated example, the eyewear 120 includes four headgear retention devices 140A-140D. However, other quantities of headgear retention devices 140A-140D, such as two (as shown in FIG. 2), three, or more. The quantity of headgear retention devices 140A-140D and the types of headgear retention devices 140A-140D can vary based on the purpose of the eyewear 120. For example, eyewear 120 produced for aviation, motorcycling, or speed boating can include more headgear retention devices 140A-140D or headgear retention devices 140A-140D that provide more tension on headgear than eyewear produced for bicycling, rowing, or baseball.

The headgear retention devices 140A-140D can be located on the headband 124 inn a way that better prevents the hat 100 from being blown from a person's head. For example, the headgear retention devices 140A and 140C are located on the headband 124 such that, when the headband 124 is properly worn over a person's head with the spectacles 122 in front of the person's eyes, the headgear retention devices 140A and 140C are in front of the person's ears, as shown in FIGS. 1A and 1B. For example, the headgear retention devices 140A and 140C can be located on the headband 124 such that, when worn, the headgear retention devices 140A and 140C are about one inch in front of the person's ears. In other examples, the headgear retention devices 140A and 140C can be between 0.5 and 1.5 inches in front of the person's ears. Other appropriate distances can be used.

To ensure such locations, the headgear retention device 140A can be located on the headband 124A a particular distance from the end 124A-1 of the band 124A and the headgear retention device 140C can be located on the headband 124B a particular distance from the end 124B-1 of the band 124B. In another example, the headgear retention device 140A can be located on the headband 124A a particular distance from the side of the spectacles 122 to which the headband 124A is attached and the headgear retention device 140C can be located on the headband 124B a particular distance from the side of the spectacles 122 to which the headband 124B is attached. This particular distance can be about one inch, e.g., between 0.5 and 1.5 inches. Other appropriate distances can also be used.

By positioning the headgear retention devices 140A and 140C in front of the person's ears and close to the front of the hat 100, the headgear retention devices 140A and 140C better prevent wind under the bill 104 of the hat 100 from moving the hat 100 relative to the wearer's head. By reducing such movement, the headgear retention devices 140A and 140C also better prevents the hat 100 from being detached from the wearer's head.

The headgear retention devices 140A-140D can be permanently, or semi-permanently, attached to the headband 124. For example, the headgear retention devices 140A-140D can be sewn or stitched onto or into the headband 124. The headgear retention devices 140A-140D can be sewn or stitched onto an outside of the headband 124, e.g., the side opposite the side of the headband 124 that touches the person's head. In this way, the headgear retention devices 140A-140D do not provide discomfort to the person wearing the headband 124. In another example, part of the headgear retention devices 140A-140D can be disposed inside of the headband 124. For example, the headband 124 can include an interior band and an exterior band. The headgear retention devices 140A-140D can be sewn or stitched between the interior and exterior bands. This configuration also prevents discomfort to the person wearing the headband 124.

In other example, the headgear retention devices 140A-140D can be removably attached to the headband 124, e.g., using double sided clips. This allows the person to remove the clips when the eyewear 120 will be worn without the hat 100 or the hat 100 will be worn in conditions with little wind or no physical activity.

The headgear retention devices 140A-140D can also be used with headbands that do not include spectacles. For example, an elastic head band can include one or more headgear retention devices in the same or similar locations as shown in FIG. 1. This elastic headband can be made of two elastic bands with a strap adjuster and the hook-and-loop fastener, similar to the headband 124.

FIG. 2 is an illustration of example eyewear 200 with headgear retention devices 240A and 240B. The example eyewear 200 includes glasses 222 attached to a headband made of two elastic bands 224A and 224B. The elastic band 224A has a first end 224A-1 that is attached to a side of the glasses 222 and a second end 224A-2 attached to a strap adjuster 230. Similarly, the elastic band 224B has a first end 224B-1 that is attached to a side of the glasses 222 and a second end 224B-2 attached to a strap adjuster 230.

The second end 224A-2 of the elastic band 224A can be attached to the strap adjuster 230 in a permanent or semi-permanent manner, e.g., such that the second end 224A-2 of the elastic band 224A cannot be easily removed from the strap adjuster 230 without a knife, scissors, or other tool. For example, the second end 224A-2 can be passed through a first aperture 230A of the strap adjuster 230 and then attached to a portion 224A-3 of the elastic band 224A that was not passed through the first aperture 230A of the strap adjuster 230. The second end 224A-2 of the elastic band 224A can be sewn to or stitched to the other portion of the elastic band 224B.

The second end 224B-2 of the elastic band 224B can be removably attached to the strap adjuster 230 in a manner that allows the size of the headband to easily be adjusted. The second end 224B-2 of elastic band 224B includes a first portion 226A that has a patch of hooks 228, e.g., a fabric strip of hooks. The second end 224B-2 of the elastic band 224B also includes a second portion 226B that has a patch of loops 229, e.g., a fabric strip of loops.

A person can pass the first portion 226A of the elastic band 224B through a second aperture 230B of the strap adjuster 230. The person can then press the patch of hooks 228 against the patch of loops 229, e.g., by pressing the first portion 226A of the elastic band 224B against the second portion 226B of the elastic band 224B, fastening the two patches temporarily. The person can adjust the size of the headband by adjusting the portion of the patch of loops 229 that is pressed against the path of hooks 228. In this way, the person can easily adjust the tightness of the headband on the person's head so that the headband is tight enough to prevent the person's hat from detaching from the person's head and so that the headband is comfortable.

In this example, the headgear retention devices 240A and 240B are clips sewn onto the elastic bands 224A and 224B, respectively. The headgear retention devices 240A and 240B are shown in the open position. When the eyewear 200 is worn around a person's head and headgear, e.g., a hat, is also worn on the person's head, the person (or another person) can put the clips around the bottom of the headgear and close the clips so that the clips are attached to the bottom of the headgear.

The headgear retention devices 240A and 240B are positioned on the elastic bands 224A and 224B, respectively, such that the headgear retention devices 240A and 240B are close to the glasses 222, e.g., within an inch of each side of the glasses 222. In this way, the headgear retention devices 240A and 240B will be attached to the front of the headgear, e.g., in front of the ears of the person wearing the headgear and the eyewear 200.

Figure 3:
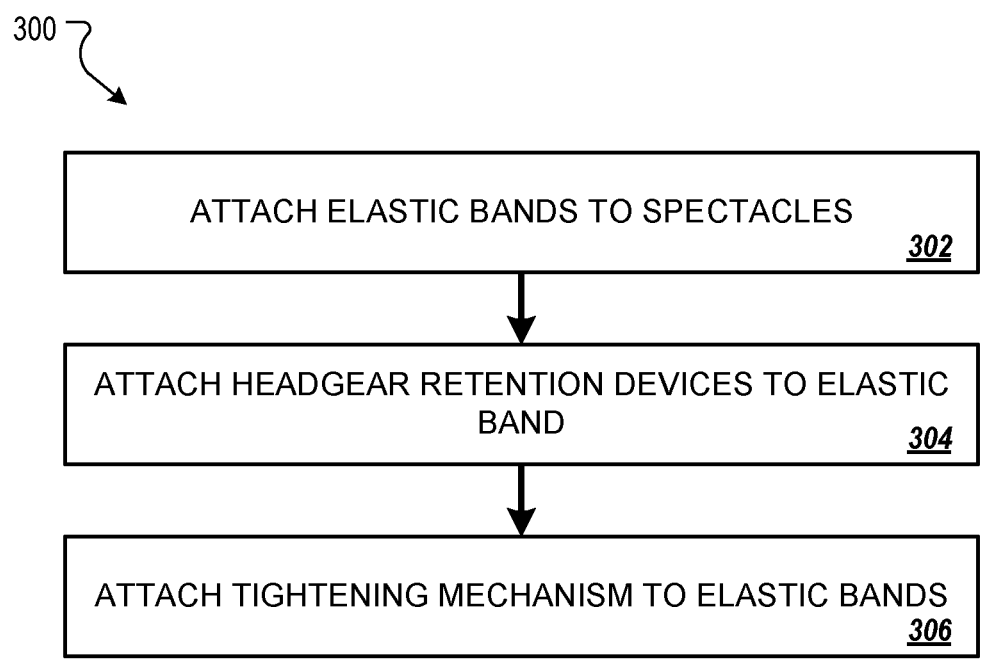
FIG. 3 is a flow diagram of an example process for assembling eyewear with headgear retention devices.

FIG. 3 is a flow diagram of an example process 300 for assembling eyewear with headgear retention devices. The example process 300 can be performed by a person and/or manufacturing equipment, e.g., automated robot arms and/or industrial sewing machines.

Elastic bands are attached to spectacles (302). As described above, the spectacles can be glasses, sunglasses, goggles, framed lenses, or other appropriate types of spectacles that are worn over a person's eyes. The elastic bands can be made of nylon, polyester, spandex, a cotton blend, a nylon and polyester blend, and/or other appropriate elastic materials that are suitable to be worn on a person's head.

The elastic bands can include two elastic bands. One end of a first elastic band can be attached to one side of the spectacles. One end of a second elastic band can be attached to the other side of the spectacles. For example, each side of the spectacles can include a headband attachment mechanism to which the end of an elastic band attaches. The headband attachment mechanism can be an aperture, e.g., a rectangular-shaped aperture, formed in a frame of the spectacles. In this example, an elastic band can be attached to the side of the spectacles by passing the end of the elastic band through the aperture and attaching the end of the elastic band to another portion of the elastic band that is not passed through the aperture.

In some implementations, the headband attachment mechanism includes releasable clips or buckles. For example, one part of a side release buckle (e.g., the catch end) can be attached to each side of the spectacles. The other part of a side release buckle (e.g., the hook end) can be attached to one end of each elastic band. To attach the end of an elastic band to the side of the spectacles, the hook end of the side release buckle can be inserted into the catch end of the side release buckle.

Headgear retention devices are attached to each elastic band (304). As described above, the headgear retention devices can include clips that clip to a hat or other headgear when worn by a person. In some implementations, the headgear retention devices are sewn or stitched into or onto the elastic bands. The headgear retention devices can also be attached to the elastic bands using adhesives or other appropriate attachment techniques. The headgear retention devices can be attached in appropriate locations on the elastic band such that at least one or more of the headgear retention devices are located in front of the person's head when the eyewear is properly worn by a person with the spectacles in front of the person's eyes.

A tightening mechanism is attached to the elastic bands (306). The tightening mechanism can include a strap adjuster that includes a respective aperture, e.g., a rectangular-shaped aperture, for each band. The strap adjuster can be a strap adjuster buckle than enables the two straps to be attached and detached to and from one another easily.

The tightening mechanism can also include a hook-and-loop fastener attached to at least one of the elastic bands. As described above, the hook-and-loop fastener enables a person to easily attach and detach the elastics bands to and from another easily. The hook-and-loop fastener also enables a person to easily adjust the tightness of the headband formed by the elastic bands. The hook-and-loop fastener can be attached to an elastic band by attaching a patch of hooks to one side of the end of the elastic band that is not attached to the spectacles. The patch of loops is attached to the same side of the elastic band as the patch of hooks, but further from the end of the elastic band that is not attached to the spectacles. For example, the two patches may be spaced apart an appropriate distance, e.g., less than a half inch or some other appropriate distance. In other examples, the patch of loops can be attached to the end of the elastic band and the patch of hooks can be further from the end than the patch of loops. The patches can be attached to the elastic band by sewing, stitching, adhesives, or another appropriate way.

The elastic band that does not include the hook-and-loop fastener can be attached to the strap adjuster in a semi-permanent or permanent manner. For example, an end of the band can be passed through an aperture of the strap adjuster and be attached to itself, e.g., using sewing, stitching, adhesives, or another appropriate attachment mechanism. The other end of this band can be attached to its side of the spectacles, as described above.

The elastic band with the hook-and-loop fastener can be attached to the strap adjuster by passing the end of the elastic band that has the hook-and-loop fastener through an aperture of the strap adjuster. This elastic band can be passed through a different aperture than the aperture through which the other elastic band was passed. The elastic band can be passed through the aperture such that only one of the patches of the hook-and-loop fastener is passed through the aperture. The two patches can then be pressed together to fasten the two patches temporarily, securing the elastic band to the strap adjuster. This elastic band can be attached to the strap adjuster by the person that is wearing or going to wear the eyewear, e.g., after obtaining the assembled eyewear.

Figure 4:
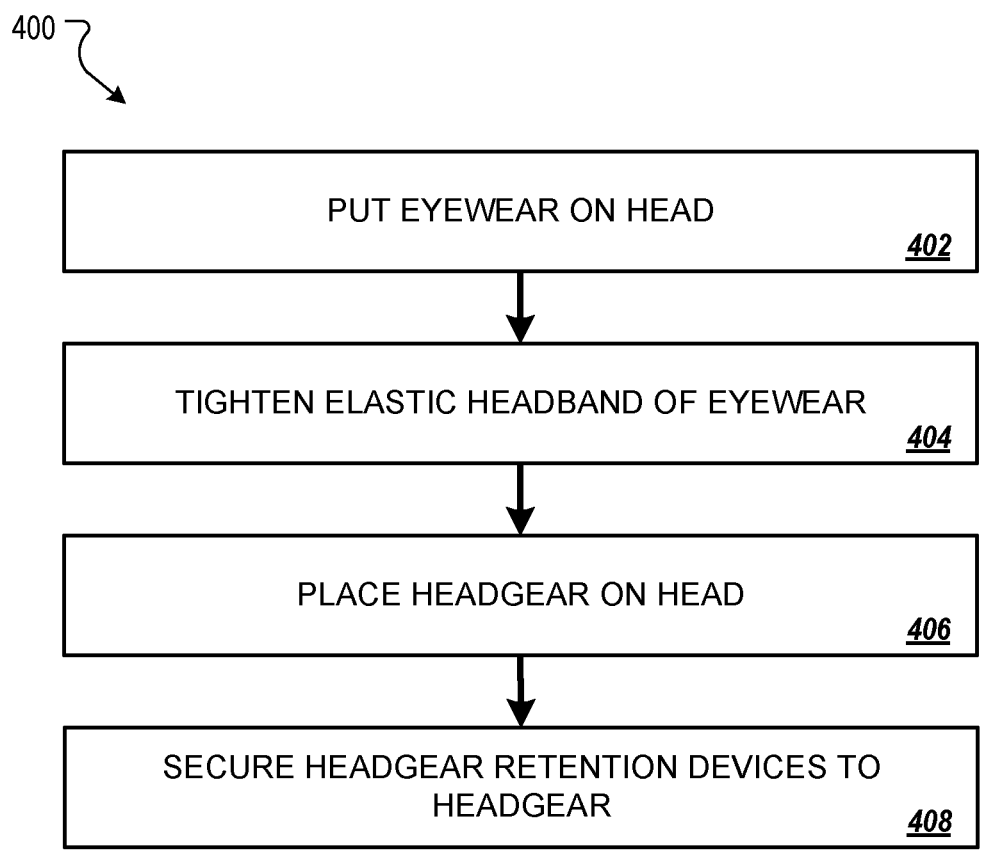
FIG. 4 is a flow diagram of an example process for using eyewear with headgear retention devices.

FIG. 4 is a flow diagram of an example process 400 for using eyewear with headgear retention devices. The process 400 can be performed by a person, e.g., the person wearing the eyewear or another person assisting the person wearing the eyewear.

The eyewear is put on a person's head (402). The eyewear can include spectacles, elastic bands, and headgear retention devices attached to the elastic bands, as described in the examples above. For example, the person can put the spectacles of the eyewear over the person's eyes and put the headband over and around the person's head.

The elastic headband is tightened around the person's head (404). As described above, one of the elastic bands of the headband can include a hook-and-loop fastener. The person can tighten the band by pulling the patch of hooks and the patch of loops apart. The person can then reposition the patch of hooks with respect to the patch of loops to adjust the tightness of the headband.

Headgear is placed on the person's head (406). For example, if the headgear is a hat, the hat can be placed on the person's head in a normal manner.

The headgear retention devices are secured to the headgear (408). As described above, the headgear retention devices can include clips. The ends of the clips can be opened and the opening of the clips can be placed around the bottom of the headgear. The clips can then be closed onto the bottom of the headgear, attaching the elastic bands to the headgear.

While this specification contains many specific implementation details, these should not be construed as limitations on the scope of any features or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Thus, particular embodiments of the subject matter have been described. Other embodiments are within the scope of the following claims.

Similarly, while operations are depicted in the drawings in a particular order, this should not be understood as requiring that such operations be performed in the particular order shown or in sequential order, or that all illustrated operations be performed, to achieve desirable results. Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

What is claimed is:

1. Eyewear, comprising:
   one or more lenses configured to be worn over eyes of a wearer;
   an elastic headband comprising a single band or two bands and configured to fit around a head of the wearer, the elastic headband being attached to each of the one or more lenses or a frame that supports the one or more lenses; and
   a plurality of headgear retention devices attached to the elastic headband and configured to be removably attached to a hat when the hat is worn on the head of the wearer and the elastic headband is worn around the head of the wearer, wherein the plurality of headgear retention devices comprises a plurality of clips comprising:
      two or more first clips attached to locations on the elastic headband such that, when the elastic headband is worn around the head of the wearer in a proper position with the one or more lenses in front of the eyes of the wearer, at least one first clip is located in front of a left ear of the wearer and at least one first clip is located in front of a right ear of the wearer; and
      two or more second clips attached to locations on the elastic headband such that, when the elastic headband is worn around the head of the wearer in the proper position with the one or more lenses in front of the eyes of the wearer, at least one second clip is located behind the left ear of the wearer and at least one second clip is located behind the right ear of the wearer,
   wherein each clip is attached to either (i) only an outside portion of the elastic headband opposite an inside portion of the elastic headband that, when the elastic headband is worn by the wearer, the inside portion of the elastic headband contacts the head of the wearer or (ii) between the outside portion and the inside portion, and
   wherein each clip is configured to open to receive a lower portion of the hat and close around the lower portion of the hat.

2. The eyewear of claim 1, further comprising goggles that include the one or more lenses.

3. The eyewear of claim 1, wherein each headgear retention device is sewn to the elastic headband.

4. The eyewear of claim 1, wherein each clip comprises a garment clip that clips to the hat.

5. The eyewear of claim 1, wherein each clip comprises an alligator clip comprising teeth configured to grip the lower portion of the hat.

6. The eyewear of claim 1, wherein each first clip is attached between 0.5 and 1.5 inches from a side of the lens or the frame to which the elastic headband is attached.

7. The eyewear of claim 1, wherein each first clip is attached 0.5 inches from a side of the lens or the frame to which the elastic headband is attached.

8. The eyewear of claim 1, wherein each first clip is attached one inch from a side of the lens or the frame to which the elastic headband is attached.

9. The eyewear of claim 1, further comprising a first headband attachment mechanism located on a first side of the one or more lenses and a second headband attachment mechanism located on a second side of the one or more lenses, wherein the second side is opposite the first side, wherein the elastic headband includes two separate bands including a first band and a second band, each band having a first end and a second end, and wherein the first end of each band attaches to a respective one of the headband attachment mechanisms.

10. The eyewear of claim 9, wherein:
   the second end of the first band is attached to a strap adjuster; and
   the second end of the second band includes a hook-and-loop fastener for removably attaching the second band to the strap adjuster.

\* \* \* \* \*